US011110363B1

(12) United States Patent
Siddi (10) Patent No.: US 11,110,363 B1
(45) Date of Patent: Sep. 7, 2021

(54) INTRAVENOUS POLE ACCESSORY (71) Applicant: Puffaluffs, Inc., Albany, NY (US)

(72) Inventor: Alfred Siddi, Albany, NY (US)

(73) Assignee: Puffaluffs, Inc., Albany, NY (US)

( * ) Notice: Subject to any disclaimer, the term of this patent is extended or adjusted under 35 U.S.C. 154(b) by 0 days.

(21) Appl. No.: 17/175,734

(22) Filed: Feb. 15, 2021

(51) Int. Cl.
*A63H 3/00* (2006.01)
*A63H 3/02* (2006.01)
*A63H 3/50* (2006.01)
*A61M 5/14* (2006.01)

(52) U.S. Cl.
CPC .......... *A63H 3/003* (2013.01); *A61M 5/1415* (2013.01); *A63H 3/02* (2013.01); *A63H 3/50* (2013.01); *A61M 2205/59* (2013.01)

(58) Field of Classification Search
CPC .......... A63H 3/003; A63H 3/005; A63H 3/00
USPC .............................. 446/72–74, 296
See application file for complete search history.

(56) References Cited

U.S. PATENT DOCUMENTS

| | | | | |
|---|---|---|---|---|
| 4,902,261 A | * | 2/1990 | Pratt | A61J 9/00 215/11.1 |
| 5,059,149 A | * | 10/1991 | Stone | A63H 3/003 446/73 |
| 5,326,300 A | * | 7/1994 | Senders | A45C 15/00 190/1 |
| 6,146,722 A | * | 11/2000 | Slawin | A47G 1/0616 40/791 |
| 6,165,035 A | * | 12/2000 | Avner | A61B 1/227 446/369 |
| D442,278 S | | 5/2001 | Rury | |
| 6,279,167 B1 | * | 8/2001 | Johnson | A42B 1/004 2/209.11 |
| 6,322,539 B1 | | 11/2001 | Cook | |
| 6,350,169 B1 | * | 2/2002 | Holt | A63H 3/005 446/327 |
| 7,556,226 B2 | | 7/2009 | Muncie | |
| 7,559,104 B1 | * | 7/2009 | Kahrig | A47D 13/08 297/181 |
| 10,039,992 B2 | | 8/2018 | Rivera | |
| 10,238,792 B1 | * | 3/2019 | Macri | F16M 11/42 |
| 10,427,060 B2 | * | 10/2019 | Corwin | A61M 5/31 |
| 10,441,751 B2 | * | 10/2019 | Chang | A61M 25/02 |
| 10,456,520 B2 | * | 10/2019 | McNeill | A61G 7/0503 |
| 10,582,981 B2 | * | 3/2020 | Childs | A61G 7/0503 |
| 2004/0205875 A1 | | 10/2004 | Byrne et al. | |
| 2006/0011786 A1 | * | 1/2006 | Finney | A47C 7/72 248/118 |
| 2006/0089077 A1 | * | 4/2006 | Wittschen | A61J 15/0026 446/77 |

(Continued)

*Primary Examiner* — Kurt Fernstrom
(74) *Attorney, Agent, or Firm* — Pablo Meles (57) ABSTRACT

An intravenous pole accessory (30) includes a stuffed doll having a head portion (32) and a main portion (33) that covers a major portion of an intravenous pole (36) upon placement of the accessory on the intravenous pole. The accessory can include at least a first attachment member (31 or 31A) coupled to a portion (32) of the stuffed doll configured and arranged for retaining the stuffed doll in a vertical position when the first attachment member is attached to a top portion (36A) of the intravenous pole, and a hole (34) in the main portion of the stuffed doll configured to allow access to a medical device (37) attached to the intravenous pole when the at least first attachment member is attached to the top portion of the intravenous pole.

20 Claims, 5 Drawing Sheets

(56) References Cited

U.S. PATENT DOCUMENTS

| | | | |
|---|---|---|---|
| 2006/0160458 A1* | 7/2006 | Peach | A63H 3/36 |
| | | | 446/72 |
| 2008/0096459 A1* | 4/2008 | Mingle | A61J 1/16 |
| | | | 446/74 |
| 2008/0139076 A1 | 6/2008 | Frasier-Scott | |
| 2010/0243834 A1 | 9/2010 | Salser | |
| 2013/0331000 A1* | 12/2013 | Drozdowski | A63H 3/02 |
| | | | 446/297 |
| 2016/0199745 A1* | 7/2016 | Powell | A63H 3/02 |
| | | | 446/73 |
| 2017/0246546 A1* | 8/2017 | Brown, Sr. | A63H 3/02 |
| 2019/0192980 A1* | 6/2019 | Vogel | A44B 1/20 |
| 2020/0146933 A1 | 5/2020 | Casano | |

\* cited by examiner

INTRAVENOUS POLE ACCESSORY

CROSS-REFERENCE TO RELATED APPLICATIONS

Not applicable.

TECHNICAL FIELD

The present disclosure is directed to an apparatus and system for concealing, hiding, or therapeutically mitigating an intimidation factor or fear factor of medical equipment or supplies using an intravenous (IV) pole accessory.

BACKGROUND

Children and adults commonly receive IV infusions or injections but are intimidated or fearful of the environment including the medical equipment and supplies that might be associated with an IV pole. Children are particularly afraid of IV bags and associated medical pumps and monitors that appear ever present for extended periods of time during an illness or recovery or treatment for an illness. Current solutions to this problem do not significantly conceal the IV pole or sufficiently reduce the intimidation factor of such medical devices.

One attempted solution comes in the form of a therapeutic pouch for concealing an intravenous therapy dispenser (such as an IV bag or other delivery apparatus of medicinal or blood product for delivery directly into the veins of a user of intravenous therapy). The therapeutic pouch can embody a stuffed animal that conceals the dispenser to the recipient of the intravenous therapy, but fails to conceal a significant portion of the IV pole or fails to reduce the intimidation factor of other medical equipment coupled to the IV pole such as pumps and monitors.

DETAILED DESCRIPTION

In some embodiments, an intravenous pole accessory can include a stuffed doll that covers a major or a majority portion of an intravenous pole upon placement on the intravenous pole, a first adjustable attachment strap coupled to a top portion of the stuffed doll configured and arranged for retaining the stuffed doll in a vertical position when the first adjustable attachment strap is attached to a top portion of the intravenous pole, and a hole in a mid-section of the stuffed doll configured to allow access to a medical device attached to the intravenous pole when the first adjustable attachment strap is attached to the top portion of the intravenous pole.

In some embodiments, the accessory further includes a rear adjustable strap on a rear portion of the stuffed doll and configured to prevent lateral movement of the stuffed doll relative to the intravenous pole when the rear adjustable strap is coupled to a vertical portion of the intravenous pole. In some embodiments, the accessory further includes a second adjustable attachment strap coupled to the top portion of the stuffed doll configured and arranged with the first adjustable attachment strap to retain the stuffed doll in the vertical portion when the first adjustable attachment strap and the second adjustable attachment strap are coupled to the top portion of the intravenous pole, where the top portion of the intravenous pole includes a horizontal segment. In some embodiments first and second adjustable straps are adjustable using either hook and loop fasteners or snap connectors. In yet other embodiments, the first and second adjustable straps are sashes that are adjustable in length based on where a user ties the sashes. In yet other embodiments, the first and second adjustable straps further include hooks or carabiner clips attached to respective ends of the first and second adjustable straps. In some embodiments, the first adjustable attachment strap is adjustable strap using hook and loop fasteners.

In some embodiments, the accessory further includes a flap for temporarily covering the hole and obscuring any device covered by the flap. In yet other embodiments, the flap is transparent or translucent, but yet covers the hole and allows monitoring of any device covered by the transparent or translucent flap.

In some embodiments, the accessory further includes a rear snap-fit member on a rear portion of the stuffed doll and configured to snap fit to a vertical portion of the intravenous pole to prevent lateral movement of the stuffed doll relative to the intravenous pole.

In some embodiments, an intravenous pole accessory includes a stuffed doll that covers a major portion of an intravenous pole upon placement on the intravenous pole, at least a first attachment member coupled to a portion of the stuffed doll configured and arranged for retaining the stuffed doll in a vertical position when the first attachment member is attached to a portion of the intravenous pole, and a hole in a mid-section of the stuffed doll configured to allow access to a medical device attached to the intravenous pole when the at least first attachment member is attached to the portion of the intravenous pole.

In some embodiments, the first attachment member is at least a first adjustable attachment strap that is adjustable using hook and loop fasteners. In some embodiments, the accessory further includes a flap for temporarily covering the hole and obscuring any device covered by the flap. In some embodiments, the flap is transparent or translucent and covers the hole yet allows for monitoring of any device covered by the transparent or translucent flap. In some embodiments, the first attachment member is at least a first rear snap-fit member on a rear portion of the stuffed doll and configured to snap fit to a vertical portion of the intravenous pole to prevent lateral and vertical movement of the stuffed doll relative to the intravenous pole.

In some embodiments, the first attachment member is at least a first rear snap-fit member on a rear portion of the stuffed doll and configured to snap fit to a vertical portion of the intravenous pole to prevent lateral movement of the stuffed doll relative to the intravenous pole.

In some embodiments, the at least first attachment member includes a first and a second adjustable strap coupled to a top portion of the stuffed doll and configured and arranged to retain the stuffed doll in a vertical portion when the first adjustable attachment strap and the second adjustable attachment strap are coupled to a top portion of the intravenous pole and where the at least first attachment member further includes s a rear adjustable strap attached to a rear portion of the stuffed doll and configured to prevent lateral movement of the stuffed doll relative to the intravenous pole when the rear adjustable strap is coupled to a vertical portion of the intravenous pole.

In some embodiments, an intravenous pole accessory includes a stuffed doll that covers a major portion of an intravenous pole upon placement on the intravenous pole, a first attachment strap and a second attachment strap coupled to a top portion of the stuffed doll, the first and second attachment straps configured and arranged for retaining the stuffed doll in a vertical position when the first and second attachment straps are attached to a top portion of the intravenous pole, a rear attachment member coupled to a rear portion of the stuffed doll, configured to attach to a vertical portion of the intravenous pole to prevent at least lateral movement of the stuffed doll relative to the intravenous pole, and a hole in a mid-section of the stuffed doll configured to allow access to a medical device attached to the intravenous pole when the first adjustable attachment strap is attached to the top portion of the intravenous pole.

In some embodiments, the stuffed doll is stuffed with non-metallic, flame retardant materials. In some embodiments, the accessory further includes a flap attached adjacent to the hole and configured to cover the medical device when the flap is in a closed position and to provide access to the medical device when the flap is in an open position.

FIGS. 1-4 illustrate various embodiments of an intravenous or IV pole accessory that can include various iterations of the embodiments intended to be within the scope of the claims. The various embodiments can include straps or other mechanism for attaching the accessory to the IV pole. In some instances, a single attachment mechanism can be used such as a single strap that will allow the accessory to hang vertically on the IV pole. In other instances two straps can be used where both are used to enable the accessory to hang vertically. In yet other instances, a single attachment mechanism can allow the IV accessory to hang vertically and another attachment mechanism in the rear and mid-section of the accessory can attach to the pole to prevent or reduce lateral movement of the accessory relative to the IV pole.

Figure 1A:
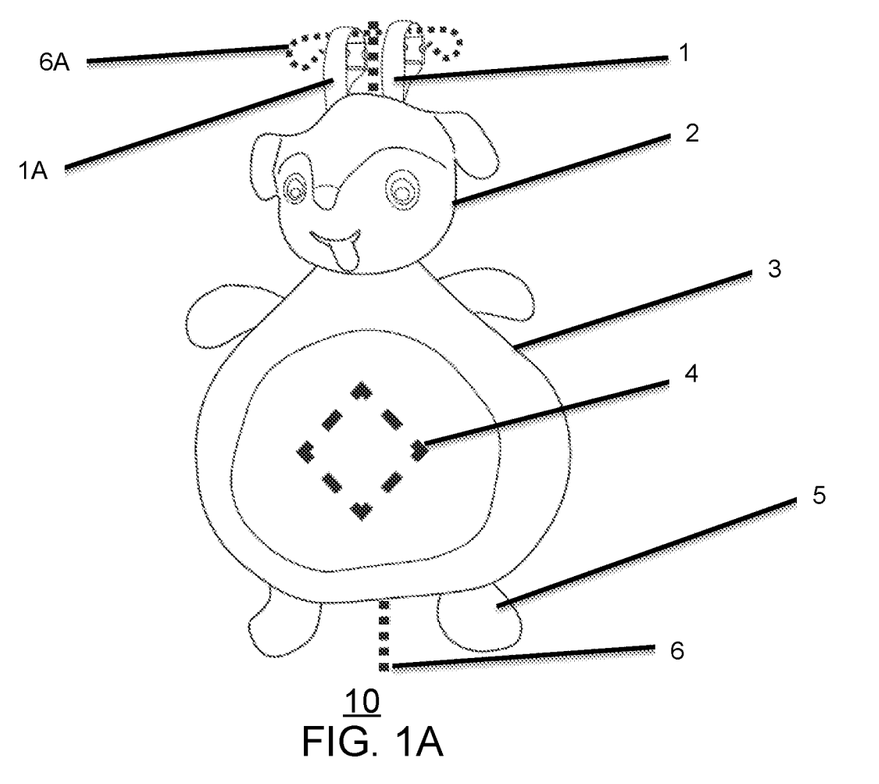
FIG. 1A illustrates a front view of an IV pole accessory hanging on an IV pole in accordance with the embodiments.
Figure 1B:
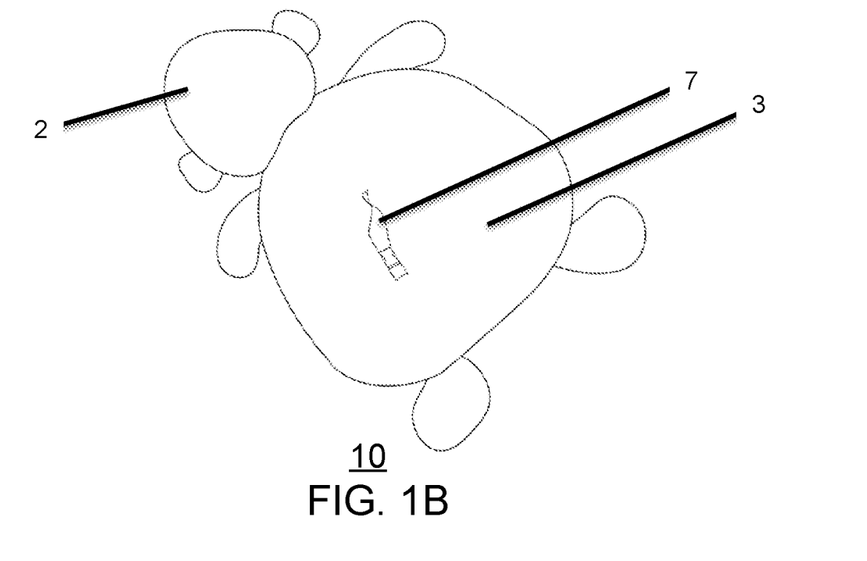
FIG. 1B illustrates a rear view of the IV pole accessory of FIG. 1A illustrating an attachment element to the IV pole in accordance with the embodiments.

Referring to FIG. 1A, an intravenous pole accessory 10 can include a stuffed doll that covers a major or a majority portion of an intravenous pole 6 upon placement of the accessory 10 on the intravenous pole 6. The stuffed doll can come in any shape such as animals, robots, or any other character. The doll forming the IV pole accessory 10 can include a head portion 2, a main body portion 3 that has a center hole or cavity 4, and a bottom portion 5 that can be feet or wheels or other typical bottom portion of a character. The accessory 10 can also include a first adjustable attachment strap 1 coupled to a top portion or head portion 2 of the stuffed doll and configured and arranged for retaining the stuffed doll in a vertical position when the first adjustable attachment strap 1 is attached to a top portion 6A of the intravenous pole 6. The hole or cavity 4 can be in central area or mid-section of the main portion 3 of the stuffed doll configured to allow access to a medical device attached to the intravenous pole 6 when the first adjustable attachment strap 1 is attached to the top portion 6A of the intravenous pole 6.

Figure 2:
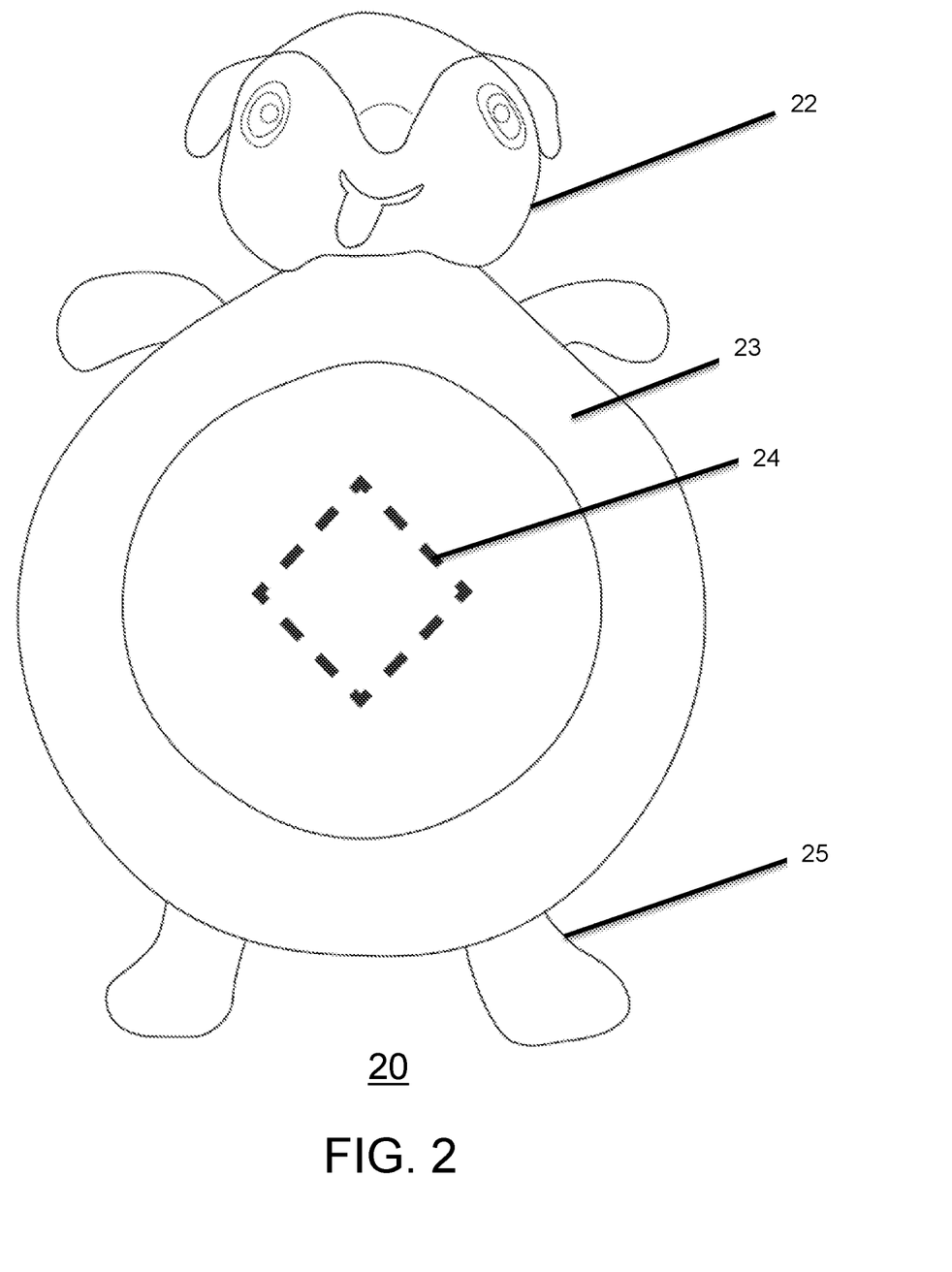
FIG. 2 illustrates yet another IV pole accessory having a center hole or viewing area in a closed position in accordance with the embodiments.

In some embodiments and with reference to FIG. 2, the accessory 10 further includes a rear adjustable strap 7 on a rear portion of the main portion 3 the stuffed doll and configured to prevent lateral movement of the stuffed doll or the accessory 10 relative to the intravenous pole 6 when the rear adjustable strap 7 is coupled to a vertical portion of the intravenous pole 6. In some embodiments, the accessory 10 further includes a second adjustable attachment strap 1A (see FIG. 1A) coupled to the top portion 2 of the stuffed doll and configured and arranged with the first adjustable attachment strap to retain the stuffed doll in the vertical portion when the first adjustable attachment strap 1 and the second adjustable 1A attachment strap are coupled to the top portion 6A of the intravenous pole 6, where the top portion of the intravenous pole includes a horizontal segment. In some embodiments first and second adjustable straps (1 and 1A) are adjustable using either hook and loop fasteners or snap connectors (see 31D of FIG. 3D). In yet other embodiments, the first and second adjustable straps (1 and 1A) are sashes that are adjustable in length based on where a user ties the sashes to the top portion 6A of the IV accessory pole 6. In yet other embodiments, the first and second adjustable straps 1 and 1A further include hooks or carabiner clips (see 31C of FIG. 3C) attached to respective ends of the first and second adjustable straps. In some embodiments, the first adjustable attachment strap is adjustable strap using hook and loop fasteners.

In some embodiments as shown in the IV accessory 20 of FIG. 2 and in other embodiments, the accessory 20 can further include a flap 24 for temporarily covering the hole (not shown) and obscuring any device covered by the flap 24. In yet other embodiments, the flap 24 is transparent or translucent, but yet covers the hole and allows monitoring of any device covered by the transparent or translucent flap 24. The IV accessory 40 of FIG. 4 more clearly illustrates a transparent or translucent flap 44.

Figures 3A, 3C, 3D, 3E, 3F:
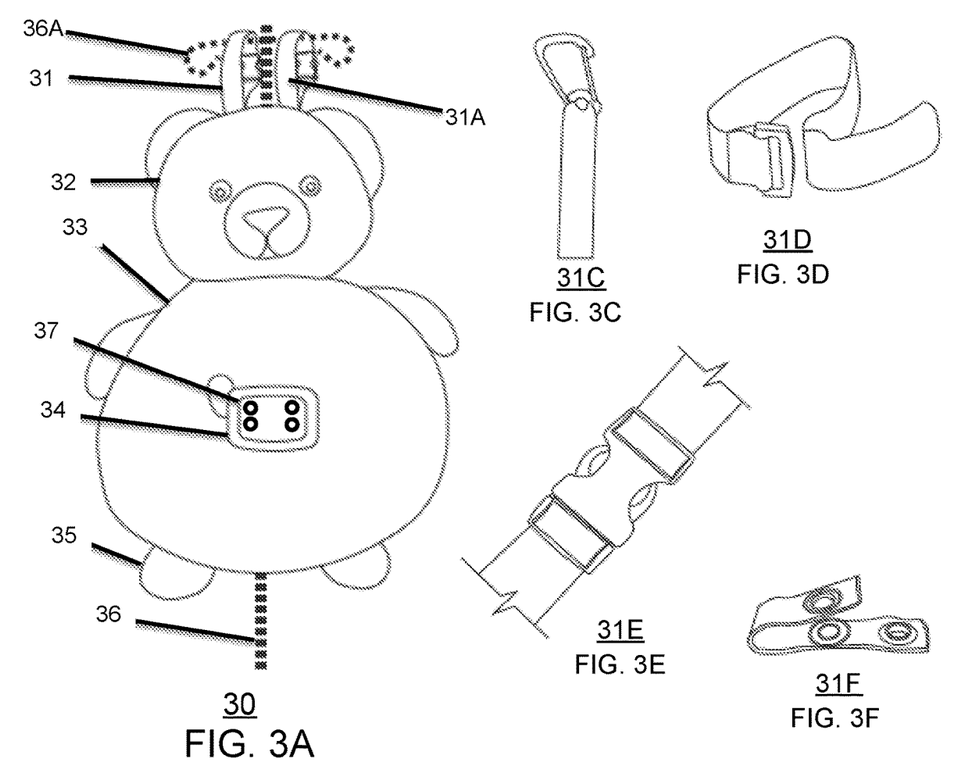
FIG. 3A illustrates a front view of another IV pole accessory hanging on an IV pole with a center hole in an open position enabling viewing and access to a medical device in accordance with the embodiments.
FIGS. 3C, 3D, 3E, 3F, and 3G illustrate different attachment elements that can be used with the IV pole accessory to attach the accessory to the IV pole in accordance with various embodiments.

In some embodiments, the accessory further includes a rear snap-fit member such as a snap fit member 31F shown in FIG. 3F that can be attached to or on a rear portion of the stuffed doll and configured to snap fit to a vertical portion of the intravenous pole (6, 36 or 46) to prevent lateral movement of the stuffed doll relative to the intravenous pole. Again, the adjustable strap members 1 or 1A in FIG. 1A, the adjustable strap 7 of FIG. 1B, the adjustable strap members 31 or 31A of FIG. 3A, the adjustable strap member 31C of FIG. 3B, or the adjustable strap members 41 or 41A of FIG. 4 can be attached to the accessory and formed from just a strap or sash, or a strap and caribiner 31C as shown in FIG. 3C, or hook and loop fasteners or Velcro™ 31D as shown in FIG. 3D, or strap with buckle 31E as shown in FIG. 3E, or snap fit member 31F as shown in FIG. 3F, or a different snap fit member 31G of FIG. 3G that can be adhered to the doll or IV accessory to enable a direct snap fit to a vertical pole portion of the IV pole.

In some embodiments as shown in FIG. 3A, an intravenous pole accessory 30 includes a stuffed doll having a head portion 32 and a main portion or mid-section 33 and feet 35 that collectively covers a major portion of an intravenous pole 36 upon placement of the accessory 30 on the intravenous pole 36. The accessory 30 can include at least a first attachment member (31 or 31A) coupled to a portion of the stuffed doll configured and arranged for retaining the stuffed doll in a vertical position when the first attachment member (31 or 31A) is attached to a portion 36A of the intravenous pole 36, and a hole 34 in the mid-section 33 of the stuffed doll configured to allow access to a medical device 37 attached to the intravenous pole 36 when the at least first attachment member (31 or 31A) is attached to the portion 36A of the intravenous pole 36.

In some embodiments, the first attachment member (31 or 31A) is at least a first adjustable attachment strap that is adjustable using hook and loop fasteners such as the one shown in FIG. 3D. In some embodiments, the accessory further includes a flap (see 44A of FIG. 4) for temporarily covering the hole (34 or 44) and obscuring any device (such as pump 37 or 47 of FIG. 3 or 4 respectively) covered by the flap 44A. In some embodiments as shown in the accessory 40 of FIG. 4, the flap 44A is transparent or translucent and covers the hole 44 yet allows for monitoring of any device (such as pump 37) covered by the transparent or translucent flap 44A. In some embodiments, the first attachment member is at least a first rear snap-fit member 31G shown in FIG. 3G attached to or on a rear portion of the stuffed doll and configured to snap fit to a vertical portion of the intravenous pole to prevent lateral and vertical movement of the stuffed doll relative to the intravenous pole. In some embodiments, the snap-fit member 31G can replace the strap or straps that would be used on the rear mid-section of the doll or IV accessory. In some embodiments, the snap-fit member 31G can be used alone as the only attachment mechanism that attaches the doll or accessory to the IV pole (obsoleting the use of the straps holding the doll vertically as well in certain instances).

In some embodiments, the first attachment member is at least a first rear snap-fit member (31F of FIG. 3F or 31G of FIG. 3G) on a rear portion of the stuffed doll and configured to snap fit to a vertical portion of the intravenous pole (36 or 46) to prevent lateral movement of the stuffed doll or accessory relative to the intravenous pole.

Figure 3B:
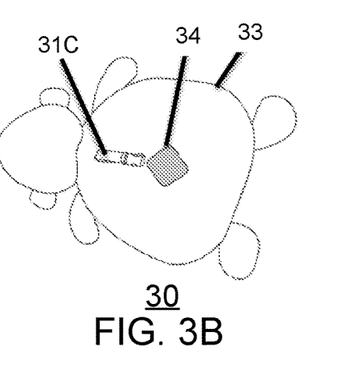
FIG. 3B illustrates a rear view of the IV pole accessory of FIG. 3A illustrating an attachment element to the IV pole in accordance with the embodiments.
Figure 3G:
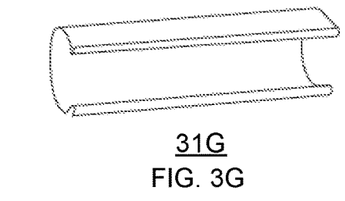

In some embodiments as shown in FIGS. 3A and 3B, the at least first attachment member includes a first and a second adjustable strap 31 and 31A coupled to a top portion 32 of the stuffed doll and configured and arranged to retain the stuffed doll or accessory 30 in a vertical position when the first adjustable attachment strap 31 and the second adjustable attachment strap 31A are coupled to the top portion 36A of the intravenous pole 36 and where the at least first attachment member further includes a rear adjustable strap 31C attached to a rear portion of the stuffed doll and configured to prevent lateral movement of the stuffed doll (or accessory 30) relative to the intravenous pole 36 when the rear adjustable strap 31C is coupled to a vertical portion of the intravenous pole 36.

Figure 4:
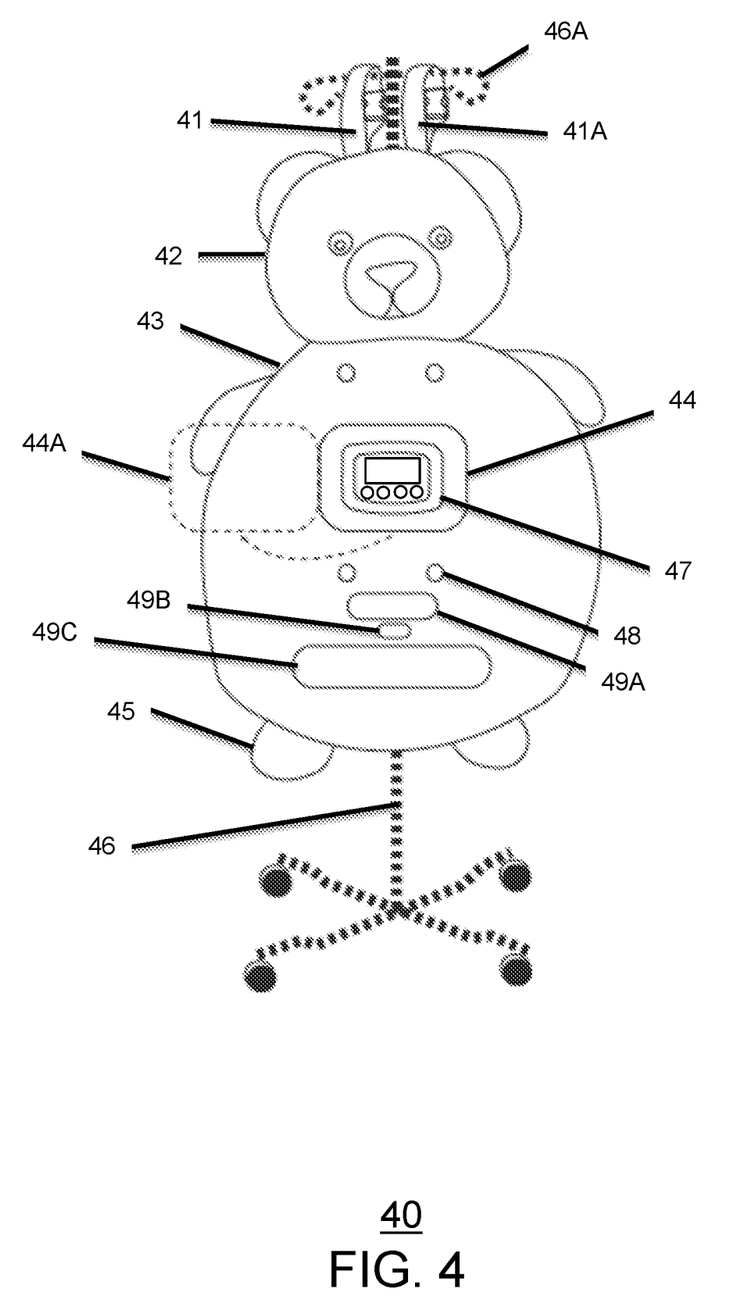
FIG. 4 illustrates a front view of another IV pole accessory hanging on an IV pole with a center hole in an open position enabling viewing and access to a medical device in accordance with the embodiments.

In some embodiments as shown in FIG. 4, an intravenous pole accessory 40 includes a stuffed doll that covers a major or a majority portion of an intravenous pole 46 upon placement of the accessory 40 on the intravenous pole 46, a first attachment strap 41 and a second attachment strap 41A coupled to a top portion 42 of the stuffed doll (40), the first and second attachment straps (41 and 41A) configured and arranged for retaining the stuffed doll (40) in a vertical position when the first and second attachment straps (41 and 41A) are attached to a top portion 46A of the intravenous pole 46, a rear attachment member (not shown) coupled to a rear portion of the stuffed doll, configured to attach to a vertical portion of the intravenous pole 46 to prevent at least lateral movement of the stuffed doll (40) relative to the intravenous pole 46, and a hole 44 in a mid-section 43 of the stuffed doll configured to allow access to a medical device (such as IV pump 47) attached to the intravenous pole 46 when the first adjustable attachment strap (41 or 41A) is attached to the top portion 46A of the intravenous pole 46.

In some embodiments, the stuffed doll of the accessory 40 is stuffed with non-metallic, flame retardant materials. The non-metallic materials will serve to avoid interfering with any wireless signaling that may be occurring between the medical device 47 and other devices that may be in communication with the medical device (such as a wireless router or gateway). In some embodiments, the accessory 40 further includes a flap 44A attached adjacent to the hole 44 and configured to cover the medical device 47 when the flap 44A is in a closed position and to provide access to the medical device 47 when the flap 44A is in an open position.

In some embodiments, the IV accessory 40 can include other user input or output devices that are embedded in the doll or IV accessory 40 such as LED indicator lights 48, a speaker 49A, a microphone 49B, and/or a display 49C. In some embodiments, the speaker and microphone can be coupled to an artificial intelligence system that uses voice recognition such as Alexa by Amazon or Siri by Apple Computer. The artificial intelligence systems can communicate with the patient and further distract the patient from the medical devices and treatment being administered.

Figure 5:
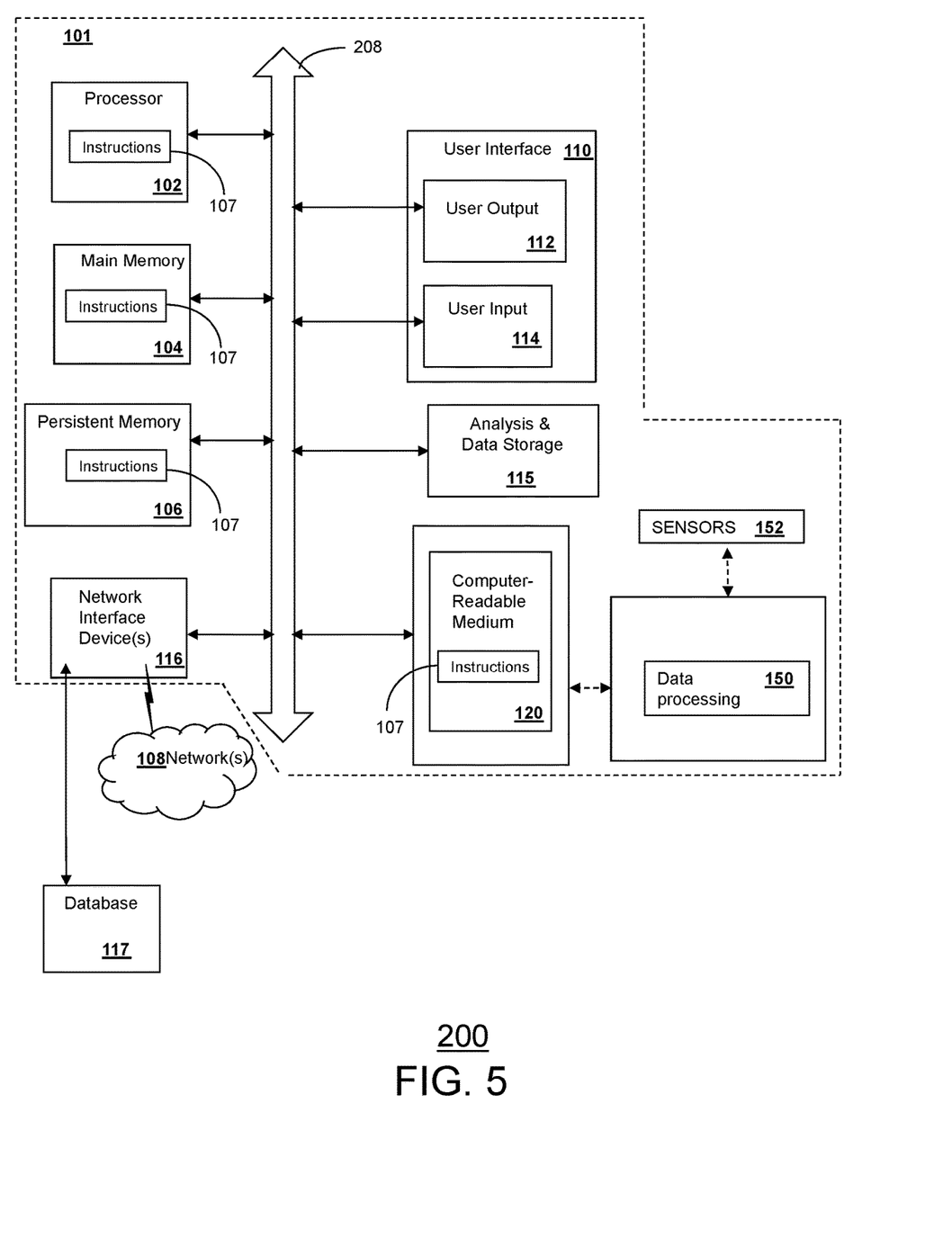
FIG. 5 is a block diagram of a system in accordance with the embodiments.

In some embodiments, and with further references to FIG. 5, a system 200 used in conjunction with the IV accessory can include any number and combination of the previously described components above as well as one or more processors which when executing the computer instructions, performs the functions of distracting or even assisting a patient under duress due to the intimidating nature of such medical equipment associated with IV poles.

In some embodiments, the system can utilize artificial intelligence and more particularly machine learning which can use exemplary training data and/or actual commercial use data to further refine what is intended to serve as distraction or stress reliever based on a particular environment or a number of known environments. Machine learning is a method of data analysis that automates analytical model building. It is a branch of artificial intelligence based on the idea that systems can learn from data, identify patterns and make decisions with minimal human intervention. Some of the training data that can be used to help identify patterns and make decisions can include fields such as identity codes, scheduling data, location data and/or other parameters obtained from sensors such as cameras, video monitoring devices, audio devices, temperature or other sensor data that can be programmatically configured to more adequately and accurately reflect real world conditions as a system is utilized in a particular environment and hopefully across different environments. Ideally, using machine learning enables systems to automatically learn and improve from experience without being explicitly programmed. Machine learning in the embodiments herein can focus on the development of computer programs (using the Python programming language, for example) to access data and use it to learn for itself in order to better predict when a lockbox should be in either a locked or an unlocked mode.

In some embodiments, the system can be a client device having one or more computer storage mediums containing computer instructions enabling monitoring or relieving of stress levels of patients, one or more processors operationally coupled to the one or more computer storage mediums where the one or more processors perform the operations described above.

In some embodiments, the system can further include a computer-storage media coupled to a processor (or processors) and computer-executable instructions embodied in the computer-storage media that, when executed by one or more computing devices, perform a method that perform any number of steps such as performing the method of distracting a patient under stress or duress due to treatment in view of an IV pole or an IV pole having medical equipment.

Various embodiments of the present disclosure can be implemented on an information processing system. The information processing system is capable of implementing and/or performing any of the functionality set forth above. Any suitably configured processing system can be used as the information processing system in embodiments of the present disclosure. The information processing system is operational with numerous other general purpose or special purpose computing system environments, networks, or configurations. Examples of well-known computing systems, environments, and/or configurations that may be suitable for use with the information processing system include, but are not limited to, personal computer systems, server computer systems, thin clients, hand-held or laptop devices, notebook computing devices, multiprocessor systems, mobile devices, microprocessor-based systems, set top boxes, programmable consumer electronics, network PCs, minicomputer systems, mainframe computer systems, Internet-enabled television, and distributed cloud computing environments that include any of the above systems or devices, and the like. As noted previously, the data processing can be any number of data processing techniques suited for tracking repetitions of a particular exercise.

For example, a user with a mobile device may be in communication with a server configured to implement the system using the aforementioned elements, according to an embodiment of the present disclosure. The mobile device can be, for example, a multi-modal wireless communication device, such as a "smart" phone, configured to store and execute mobile device applications ("apps"). Such a wireless communication device communicates with a wireless voice or data network using suitable wireless communications protocols.

The system may include, inter alia, various hardware components such as processing circuitry executing modules that may be described in the general context of computer system-executable instructions, such as program modules, being executed by the system. Generally, program modules can include routines, programs, objects, components, logic, data structures, and so on that perform particular tasks or implement particular abstract data types. The modules may be practiced in various computing environments such as conventional and distributed cloud computing environments where tasks are performed by remote processing devices that are linked through a communications network. In a distributed cloud computing environment, program modules may be located in both local and remote computer system storage media including memory storage devices. Program modules generally carry out the functions and/or methodologies of embodiments of the present disclosure, as described above.

In some embodiments, a system includes at least one memory and at least one or more processor of a computer system communicatively coupled to the at least one memory. The at least one processor can be configured to perform a method including methods described above.

According to yet another embodiment of the present disclosure, a computer readable storage medium comprises computer instructions which, responsive to being executed by one or more processors, cause the one or more processors to perform operations as described in the methods or systems above or elsewhere herein.

As shown in FIG. 5, an information processing system 101 of a system 200 can be communicatively coupled with the data processing module 150 and a group of client or other devices, or coupled to a presentation device for display at any location at a terminal or server location. According to this example, at least one processor 102, responsive to executing instructions 107, performs operations to communicate with the processing module 150 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the data processing module 150 and more generally used by the information processing system 200. The data processing module 150 can be coupled to one or more sensors 152 as needed. Such sensors can be barcode scanners, fingerprint readers, proximity sensors, microphones, cameras, video cameras, location sensors, motion detectors, scales, biometric reading devices (e.g., iris scanners, facial recognition scanners, voice detection devices) and other devices as contemplated herein. Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The data processing module 150, and the information processing system 200, can use the information from the history log such as in the analysis process and in making decisions related to a particular user's stress or anxiety levels according to a database of best practices for a particular procedure or procedures.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 200 includes a user interface (or interfaces) 110 that comprises a user output interface 112 and user input interface 114. Examples of elements of the user output interface 112 can include a display, a speaker, one or more indicator lights, one or more transducers that generate audible indicators, and a haptic signal generator or any of the interfaces illustrated or discussed with respect to the figures or elsewhere in the application. Examples of elements of the user input interface 114 can include a keyboard, a keypad, a mouse, a track pad, a touch screen, a touch pad, a microphone that receives audio signals, a camera, a video camera, a CT-Scanner, or any other scanner that scans images. Some user inputs can be sensors or vice-versa. The received audio signals or scanned images, for example, can be converted to electronic digital representations and stored in memory, and optionally can be used with corresponding voice or image recognition software executed by the processor 102 to receive user input data and commands, or to receive test data for example. The voice recognition software can be used to enter or check off items on a checklist and further provide data or text entry allowing a patient or even a caregiver to enter notes as needed.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

FIGS. 1-4 illustrate examples of systems, methods or process flows, according to various embodiments of the present disclosure, which can operate in conjunction with the information processing system 200 of FIG. 5.

The invention claimed is:

1. An intravenous pole accessory, comprising:
  a stuffed doll that covers a majority portion of an intravenous pole upon placement on the intravenous pole;
  a first adjustable attachment strap coupled to a top portion of the stuffed doll configured and arranged for retaining the stuffed doll in a vertical position when the first adjustable attachment strap is attached to a top portion of the intravenous pole; and
  a hole in a mid-section of the stuffed doll configured to allow access to monitor and operate an electronic medical device attached to the intravenous pole when the first adjustable attachment strap is attached to the top portion of the intravenous pole.

2. The intravenous pole accessory of claim 1, wherein the accessory further comprises a rear adjustable strap on a rear portion of the stuffed doll and configured to prevent lateral movement of the stuffed doll relative to the intravenous pole when the rear adjustable strap is coupled to a vertical portion of the intravenous pole.

3. The intravenous pole accessory of claim 1, wherein the accessory further comprises a second adjustable attachment strap coupled to the top portion of the stuffed doll configured and arranged with the first adjustable attachment strap to retain the stuffed doll in a vertical portion when the first adjustable attachment strap and the second adjustable attachment strap are coupled to the top portion of the intravenous pole, wherein the top portion of the intravenous pole includes a horizontal segment.

4. The intravenous pole accessory of claim 3, wherein the first and second adjustable straps are adjustable using either hook and loop fasteners or snap connectors.

5. The intravenous pole accessory of claim 3, wherein the first and second adjustable straps are sashes that are adjustable in length based on where a user ties the sashes.

6. The intravenous pole accessory of claim 3, wherein the first and second adjustable straps further include hooks or carabiner clips attached to respective ends of the first and second adjustable straps.

7. The intravenous pole accessory of claim 1, wherein the first adjustable attachment strap is an adjustable strap using hook and loop fasteners.

8. The intravenous pole accessory of claim 1, wherein the electronic medical device is a pump and wherein the accessory further comprises a flap for temporarily covering the hole and obscuring the pump covered by the flap.

9. The intravenous pole accessory of claim 1, wherein the accessory further comprises a transparent or translucent flap for covering the hole and yet allowing monitoring of any device covered by the transparent or translucent flap.

10. The intravenous pole accessory of claim 1, wherein the accessory further comprises a rear snap-fit member on a rear portion of the stuffed doll and configured to snap fit to a vertical portion of the intravenous pole to prevent lateral movement of the stuffed doll relative to the intravenous pole.

11. An intravenous pole accessory, comprising:
  a stuffed doll that covers a majority portion of an intravenous pole upon placement on the intravenous pole;
  at least a first attachment member coupled to a portion of the stuffed doll configured and arranged for retaining the stuffed doll in a vertical position when the first attachment member is attached to a portion of the intravenous pole; and
  a hole in a mid-section of the stuffed doll configured to allow access to monitor and operate an electronic medical device attached to the intravenous pole when the at least first attachment member is attached to the portion of the intravenous pole.

12. The intravenous pole accessory of claim 11, wherein the at least first attachment member is at least a first adjustable attachment strap using hook and loop fasteners.

13. The intravenous pole accessory of claim 11, wherein the accessory further comprises a flap for temporarily covering the hole and obscuring any device covered by the flap.

14. The intravenous pole accessory of claim 11, wherein the accessory further comprises a transparent or translucent flap for covering the hole and yet allowing monitoring of any device covered by the transparent or translucent flap.

15. The intravenous pole accessory of claim 11, wherein the first attachment member is at least a first rear snap-fit member on a rear portion of the stuffed doll and configured to snap fit to a vertical portion of the intravenous pole to prevent lateral and vertical movement of the stuffed doll relative to the intravenous pole.

16. The intravenous pole accessory of claim 11, wherein the first attachment member is at least a first rear snap-fit member on a rear portion of the stuffed doll and configured to snap fit to a vertical portion of the intravenous pole to prevent lateral movement of the stuffed doll relative to the intravenous pole.

17. The intravenous pole accessory of claim 11, wherein the at least first attachment member includes a first and a second adjustable strap coupled to a top portion of the stuffed doll and configured and arranged to retain the stuffed doll in a vertical portion when the first adjustable attachment strap and the second adjustable attachment strap are coupled to a top portion of the intravenous pole and wherein the at least first attachment member further includes s a rear adjustable strap attached to a rear portion of the stuffed doll and configured to prevent lateral movement of the stuffed doll relative to the intravenous pole when the rear adjustable strap is coupled to a vertical portion of the intravenous pole.

18. An intravenous pole accessory, comprising:
a stuffed doll that covers a majority portion of an intravenous pole upon placement on the intravenous pole;
a first attachment strap and a second attachment strap coupled to a top portion of the stuffed doll, the first and second attachment straps configured and arranged for retaining the stuffed doll in a vertical position when the first and second attachment straps are attached to a top portion of the intravenous pole;
a rear attachment member coupled to a rear portion of the stuffed doll, configured to attach to a vertical portion of the intravenous pole to prevent at least lateral movement of the stuffed doll relative to the intravenous pole; and
a hole in a mid-section of the stuffed doll configured to allow access to a medical device in wireless communication with a wireless router or gateway and attached to the intravenous pole when the first adjustable attachment strap is attached to the top portion of the intravenous pole.

19. The intravenous pole of claim 18, wherein the stuffed doll is stuffed with non-metallic, flame retardant materials that avoids interfering with any wireless signaling that occurs between the medical device and other devices in communication with the medical device.

20. The intravenous pole of claim 18, wherein the accessory further comprises a speaker and microphone coupled to an artificial intelligence system using voice recognition.

* * * * *